(12) United States Patent
Sohn et al.

(10) Patent No.: US 8,344,173 B2
(45) Date of Patent: Jan. 1, 2013

(54) DENDRITIC OLIGOPEPTIDE-GRAFTEDED CYCLOTRIPHOSPHAZENE, A PROCESS FOR THE PREPARATION THEREOF AND A DRUG DELIVERY SYSTEM CONTAINING THE SAME

(75) Inventors: Youn Soo Sohn, Seoul (KR); Yong Joo Jun, Seoul (KR); Sung Mo Choi, Seoul (KR)

(73) Assignee: CnPharm Co., Ltd., Seoul (KR)

( * ) Notice: Subject to any disclaimer, the term of this patent is extended or adjusted under 35 U.S.C. 154(b) by 251 days.

(21) Appl. No.: 12/990,089

(22) PCT Filed: Apr. 28, 2009

(86) PCT No.: PCT/KR2009/002190
§ 371 (c)(1),
(2), (4) Date: Oct. 28, 2010

(87) PCT Pub. No.: WO2009/134042
PCT Pub. Date: Nov. 5, 2009

(65) Prior Publication Data
US 2011/0046347 A1  Feb. 24, 2011

(30) Foreign Application Priority Data

Apr. 28, 2008  (KR) .................. 10-2008-0039350
Apr. 24, 2009  (KR) .................. 10-2009-0036226

(51) Int. Cl.
*C07C 271/12* (2006.01)
*C07K 5/00* (2006.01)
(52) U.S. Cl. ............... 560/24; 560/29; 530/330; 568/12

(58) Field of Classification Search .................... 560/24, 560/29; 530/330; 568/12
See application file for complete search history.

(56) References Cited

FOREIGN PATENT DOCUMENTS

| KR | 1020010045493 | 6/2001 |
| KR | 1020020015180 | 2/2002 |
| WO | WO 2006/043757 | 4/2006 |

OTHER PUBLICATIONS

Yong Joo Jun et al, Bioorganic Medicinal Chemistry Letters, 17, 2007, 2975-2978.*
International Search Report for PCT/KR2009/002190, mailed Dec. 17, 2009.

* cited by examiner

*Primary Examiner* — Shailendra Kumar
(74) *Attorney, Agent, or Firm* — Nixon & Vanderhye PC (57) ABSTRACT

A cyclotriphosphazene represented by Formula 1 prepared by introducing a dendritic tetrapeptide and a hydrophilic polyethylene glycol into a cyclotriphosphazene ring, a method of preparing the same, and a drug carrier including the cyclotriphosphazene of Formula 1.

The compound according to the present invention may form a strong molecular hydrogel in a very low concentration of 2 w/w % or less. Furthermore, the hydrogel prepared using the compound of Formula 1 exhibits biodegradability, thermosensitivity at around body temperature, biocompatibility with protein drugs, and an easy way to prepare along with a sustained release property without any burst effect in the early stage of release. Therefore, the present cyclotriphosphazene molecular hydrogel may be efficiently used as a drug carrier for a sustained release of a drug, particularly, a protein drug.

10 Claims, 4 Drawing Sheets

DENDRITIC OLIGOPEPTIDE-GRAFTEDED CYCLOTRIPHOSPHAZENE, A PROCESS FOR THE PREPARATION THEREOF AND A DRUG DELIVERY SYSTEM CONTAINING THE SAME

This application is the U.S. national phase of International Application No. PCT/KR2009/002190 filed 27 Apr. 2009, which designated the U.S. and claims priority to KR Application No. 10-2008-0039350 filed 28 Apr. 2008; and KR Application No. 10-2009-0036226 filed 24 Apr. 2009, the entire contents of each of which are hereby incorporated by reference.

TECHNICAL FIELD

The present invention relates to a dendritic oligopeptide-grafted cyclotriphosphazene capable of forming a molecular hydrogel, a process of preparing the same, and a drug delivery system including the dendritic oligopeptide-grafted cyclotriphosphazene, and more particularly, to a dendritic oligopeptide-grafted cyclotriphosphazene that is capable of forming a strong hydrogel even in a very low concentration, exhibiting a release profile of the approximate zero-order, and displaying a sustained release property of a protein drug, a method of preparing the same, and a drug carrier including the dendritic oligopeptide-grafted cyclotriphosphazene.

BACKGROUND ART

Conventional organic polymer hydrogels are formed by amphiphilic (hydrophilic and hydrophobic) polymers through chemical or physical interactions among the polymer molecules in aqueous solution, thereby forming a three-dimensional cross-linked net work, which absorbs water molecules into the void of the net work, affording an intermediate mechanical and physicochemical properties between the liquid and solid phases that does not flow. Hydrogels are classified into chemical hydrogels formed by chemical crosslinking among the polymer molecules having at least two functional groups and physical hydrogels formed by random physical cross-linking through hydrogen bonding, coordinate bonding, or hydrophobic interactions. A physical hydrogel is defined as a material having solid-like fluid properties and including water at equilibrium so that it is not dissolved in water (Nayak, S.; Lyon, L. A., Angew. Chem. Int. Ed. 2005, 44, 7686).

Unlike such conventional hydrogels formed by random crosslinking of amphiphilic polymers, the molecular hydrogel that is one of the most important emerging biomaterials initially developed during the last decade was reported to have a molecular weight far less than conventional polymers (Mw>10,000) and is formed by self-assembled molecular or nano-sized fibrillar networks (SAFINs), thereby absorbing a massive amount of water molecules (Weiss, R. G.; Terech, P, Molecular Gels p 1-9, Springer: Dordrecht, The Netherlands, 2006). Generally, a gel is obtained by dissolving a small amount of a gelator in a solvent (0.1-20 w/w %) and heating or cooling the solution until it does not flow. In this regard, the temperature at which the solution stops flowing is regarded as a gelation temperature ($T_{gel}$), and a minimum concentration for forming a gel is regarded as a gelation concentration ($C_{gel}$). While conventional organic polymer hydrogels have a high gelation concentration in the range of 15 to 30 w/w % of aqueous solution, molecular hydrogels have a gelation concentration of 1 w/w % or less.

A gelator is dissolved in water to form a hydrogel with a secondary structure in the range of a nanosize ($10^{-9}$ m) to a microsize ($10^{-8}$ m). The secondary structure is in the form of agglomerate having various shapes according to the molecular structure of the unimer, such as micellar, fibrous, ribbon-type, and plate-type. Recently, diverse researches have been conducted into behaviors of amphiphilic polymers. As described above, agglomerated particles with various shapes have been observed (Fuhrhop, J. H.; Helfrich, W. Chem. Rev. 1993, 93, 1565). Particularly, diverse research into amphiphilic polymers has been conducted with respect to gelation by crosslinking among micelles. For example, researches into a triblock copolymer including polyethylene glycol (PEG) and polypropylene glycol (PPG) (PEG-PPG-PEG) such as poloxamer (ICI) ((Jorgensen, E. B.; Havidt, S.; Brown, W.; Schillen, K. Macromolecules 1997, 30, 2355) and a diblock copolymer such as PEG-PPG (Cohn, D.; Sosnik, A.; Levy, A. Biomaterials 2003, 24, 3707) and polaxamer-polyacrylic acid (PAA) (Bromgberg, L. Langmuir 1999, 15, 6792) have been conducted.

Also, research into a gel formed by micellar aggregation has been conducted. For example, according to a result of research into a copolymer of polyethylene glycol and polyester, particularly, a triblock copolymer including polyethylene glycol-poly(lactic acid-glycolic acid)-polyethylene glycol (PEG-PLGA-PEG), the size of micelles and an aggregation number rapidly increase during sol-gel transition, and accordingly interaction between polymer molecules increases to cause a phase transition.

In addition, research into a phase transition of stimulus-sensitive hydrogels caused by diverse external stimuli such as chemical (pH) and physical (temperature and light) stimuli has been conducted. Particularly, research into thermosensitive gelling, i.e., thermogelling, has been conducted. A phase transition of polyethylene glycol-poly(lactic acid-glycolic acid)-polyethylene glycol (PEG-PLGA-PEG (550-2810-550)) in aqueous solution by thermogelling is closely related to its concentration and temperature. The phase transition occurs in the order of transparent solution>turbid solution>translucent solution>opaque gel as the temperature increases (Jeong, B.; Bae, Y. H.; Kim, S. W. Macromolecules 1999, 32, 7064). Currently, research has been conducted for wide applications of thermosensitive polymers to biomedical materials mainly used as a drug delivery system, the environment, biology, and cosmetics. For example, poly(N-isopropyl acrylamide) or polyethylene oxide copolymers, hydroxy polymers, and a few polyphosphazenes were reported to exhibit thermosensitivity (K. Park Eds, Controlled Drug Delivery, 485 (1997)). However, since most known thermosensitive polymers are toxic and are non-degradable, they were reported to be not suitable for drug delivery. Even though the copolymer of polyethylene glycol-poly(lactic acid-glycolic acid)-polyethylene glycol has biodegradability, its degraded products are acidic enough to denature protein drugs and therefore, is not suitable for protein drug delivery.

Due to high potential in various biomedical applications active researches are progressing into smart hydro-gels. Particularly, a trend of recent drug delivery systems is to apply stimulus-sensitive polymer hydro-gels to biological materials. However, most known organic polymer hydro-gels are non-biodegradable, and suitable mechanical properties (viscosity) are obtained only in a high concentration of 20 w/w % or more. Furthermore, these conventional organic polymer hydro-gels exhibit a burst effect (>30 w/w %) in the early stage when they are employed as a drug carrier for sustained drug delivery.

Meanwhile, the present inventors have found that the amphiphilic compounds prepared by grafting equimolar hydrophilic polyethylene glycol (PEG) and hydrophobic linear oligopeptide into cyclotriphosphazene forms strong spherical micelles by self-assembly in aqueous solution (Youn Soo Sohn, et al., Angew. Chem. Int. Edit. 2006, 45, 6173-6176; WO 06/043757). However, these cyclotriphosphazene micelles are thermosensitive but do not form a cross-linked network because the hydrophobic linear oligopeptide groups grafted to the cyclic phosphazene ring are efficiently oriented into the micelle core and not allowed for further hydrophobic interactions to cross-link with other micelles in aqueous solution. Instead, these amphiphilic cyclotriphosphazenes exhibit a lower critical solution temperature (LCST) at which the cyclotriphosphazene micelles precipitate due to weakened hydrogen bonding between the hydrophilic surface of the micelles and solvent water molecules when the solution temperature of the cyclotriphosphazene micelles is increased. Therefore, the cyclotriphosphazene micelles bearing linear oligopeptides do not gelate but precipitate in aqueous solution when their solution temperature is increased.

DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Technical Problem

The present inventors have conducted research into a molecular hydrogel to overcome the problems of the conventional thermosensitive hydrogels described above and completed the present invention in which a dendritic tetrapeptide instead of a linear oligopeptide are introduced into cyclotriphosphazene ring along with hydrophilic polyethylene glycol.

Accordingly, the present invention provides a substance capable of forming a thermosensitive molecular hydrogel, as a protein drug carrier, having amphiphilicity (hydrophilicity/hydrophobicity), biodegradability, a sustained release property without any burst effect during the early stage of release even at a low gel concentration (<2%).

The present invention also provides a method of preparing the substance capable of forming a thermosensitive molecular hydrogel.

The present invention also provides a drug carrier including the thermosensitive molecular hydrogel.

Technical Solution

According to an aspect of the present invention, there is provided a cyclotriphosphazene represented by Formula 1 below.

Formula 1

In Formula 1, n is 7, 12, or 16, x is 0, 1, or 2, and

R is each independently a C1-C6 alkyl or benzyl.

The cyclotriphosphazene of Formula 1 may be prepared using a method comprising the reaction of a cyclotriphosphazene represented by Formula 5 below including polyethylene glycol and chlorine with an ester of a dendritic tetrapeptide represented by Formula 6 below:

Formula 5

In Formula 5, $R^1$ is $-(CH_2CH_2O)_nCH_3$.

Formula 6

In Formula 6, x and R are defined above with reference to Formula 1.

According to another aspect of the present invention, there is provided a drug carrier comprising cyclotriphosphazene represented by Formula 1.

Hereinafter, the present invention will be described in more detail.

The present inventors found that a compound represented by Formula 1 obtained by substitution with a dendritic tetrapeptide instead of the linear oligopeptide in the cyclotriphosphazene of Formula 1 disclosed in International Publication No. WO 06/043757 is capable of forming a gel having excellent mechanical strength in aqueous solution even at a low concentration of 2 w/w % or less, has biodegradability, and may be effectively used for a sustained release of a protein drug such as peptide.

According to an aspect of the present invention, there is provided a cyclotriphosphazene represented by Formula 1 below.

[Formula 1]

In Formula 1, n is 7, 12, or 16,
x is 0, 1, or 2, and
R is each independently a C1-C6 alkyl or benzyl.

The cyclotriphosphazene of Formula 1 may be selected from the group consisting of the compounds below, but is not limited thereto:

tris(methoxypolyethylene glycol350)tris[carbobenzyloxylysylaspartylbis-(diethylaspartate)]cyclotriphosphazene,
tris(methoxypolyethylene glycol550)tris[carbobenzyloxylysylaspartylbis-(diethylaspartate)]cyclotriphosphazene,
tris(methoxypolyethylene glycol750)tris[carbobenzyloxylysylaspartylbis-(diethylaspartate)]cyclotriphosphazene,
tris(methoxypolyethylene glycol350)tris[carbobenzyloxylysylglutamylbis-(diethylglutamate)]cyclotriphosphazene,
tris(methoxypolyethylene glycol550)tris[carbobenzyloxylysylglutamylbis-(diethylglutamate)]cyclotriphosphazene,
tris(methoxypolyethylene glycol750)tris[carbobenzyloxylysylglutamylbis-(diethylglutamate)]cyclotriphosphazene,
tris(methoxypolyethylene glycol350)tris[carbobenzyloxylysylaminomalonylbis-(diethylmalonate)]cyclotriphosphazene,
tris(methoxypolyethylene glycol550)tris[carbobenzyloxylysylaminomalonylbis-(diethylmalonate)]cyclotriphosphazene, and
tris(methoxypolyethylene glycol750)tris[carbobenzyloxylysylaminomalonylbis-(diethylmalonate)]cyclotriphosphazene.

According to another aspect of the present invention, there is provided a method of preparing the cyclotriphosphazene of Formula 1. The method will now be described in detail.

First, monomethoxypolyethylene glycol represented by Formula 2 is reacted with sodium metal or potassium metal to prepare a metal salt of methoxy polyethylene glycol represented by Formula 3 below.

Formula 2

Formula 3

The ratio of the compound of Formula 2 to sodium metal or potassium metal is not limited. According to an embodiment, 1.2-1.5 equivalents of sodium metal or potassium metal may be used per 1 equivalent of the compound of Formula 2. The compound of Formula 2 may be used for the reaction after moisture of the compound is removed using azotropic distillation in toluene. Any organic solvent that does not inhibit the reaction, such as tetrahydrofuran (THF), benzene, or toluene may be used for the reaction. The reaction may be performed by refluxing in an inert atmosphere, e.g., in the presence of argon gas, for about 4 hours or more.

Then, the methoxy polyethylene glycol salt of Formula 3 is reacted with a hexachlorocyclotriphosphazene represented by Formula 4 below to prepare a compound represented by Formula 5 below.

Formula 4

-continued

[Formula 5]

In Formula 5, $R^1$ is —$(CH_2CH_2O)_nCH_3$.

The reaction mole ratio of the compound of Formula 3 to the compound of Formula 4 is not limited. According to an embodiment, 3.0 to 3.9 equivalents, for example, 3.0 to 3.1 equivalents of the methoxy polyethylene glycol metal salt of Formula 3 may be reacted with 1 mol (6 equivalents) of hexachlorocyclotriphosphazene ($N_3P_3Cl_6$) of Formula 4. Any solvent that does not inhibit the reaction, for example, a solvent selected from the group consisting of tetrahydrofuran, benzene, toluene and chloroform, and any combination thereof may be used for the reaction. The solution of hexachlorocyclotriphosphazene of Formula 4 is cooled to a low temperature equal to or less than −20° C., and the solution of the methoxy polyethylene glycol metal salt of Formula 3 is slowly added thereto. For example, an intermediate of the cyclophosphazene of Formula 5 that is a cis-nongeminal isomer may be prepared by performing the reaction at a temperature equal to or less than −20° C. for 4 to 8 hours and at room temperature for 8 to 24 hours. The said reaction at −20° C. or lower may be performed in, for example, a dry ice-acetone bath (−60 to −70° C.).

Then, the cyclotriphosphazene of Formula 5 including equimolar polyethylene glycol and chlorine is reacted with an ester of a dendritic tetrapeptide represented by Formula 6 to prepare the cyclotriphosphazene of Formula 1.

[Formula 6]

In Formula 6, x and R are defined above with reference to Formula 1.

The mole ratio of the compound of Formula 5 to the compound of Formula 6 is not limited. According to an embodiment, 1.5 to 2.0 equivalents of the compound of Formula 6 may be reacted with each of the unsubstituted chlorine atoms in the compound of Formula 5. The reaction may be performed in the presence of a base, for example, triethylamine, catalyzing nucleophilic substitution of the compound of Formula 6 with the unsubstituted chlorine atoms of the compound of Formula 5. The mole ratio of the base acting as a catalyst to each of the unsubstituted chlorine atoms of the compound of Formula 5 may be a large excess, for example, 4 to 10 times. Any solvent that does not inhibit the reaction, for example, a solvent selected from the group consisting of tetrahydrofuran, benzene, toluene and chloroform, and any combination thereof may be used for the reaction. The reaction may be performed at room temperature for about 24 hours and then at a temperature in the range of 40 to 60° C. for about 3 to 4 days with refluxing.

When the reaction is completed, the compound of Formula 1, the product of the reaction may be isolated and purified. First, the reaction solution may be centrifuged or filtered to remove precipitated by-products ($Et_3NHCl$ or NaCl), and the residual solution is concentrated under reduced pressure, and then, the above-mentioned organic solvent is added thereto to dissolve the concentrate. The resultant solution is washed three times with water, and the organic layer is dried using a drying agent, for example, $MgSO_4$. The dried solution is filtered under reduced pressure, and the obtained filtrate is concentrated under reduced pressure. The concentrated product is finally purified using a normal-phase chromatography, e.g., silicagel chromatography, to obtain the final compound of Formula 1.

The tetrapeptide compound of Formula 6 may be commercially available or may be prepared from a commercially available starting material using a method known in the literature, for example, a method disclosed by John Jones, Amino Acid and Peptide Synthesis, Oxford University Press, 32-34, (1994).

An embodiment of the entire process of preparing the compound of Formula 1 is represented by Reaction Scheme 1 below.

Reaction Scheme 1

-continued (1)

In Reaction Scheme 1, M is sodium or potassium, and n, x, and R are defined above with reference to Formula 1.

The compound of Formula 1 which is prepared by introducing equimolar amounts of a dendritic tetrapeptide and a hydrophilic polyethylene glycol into cyclotriphosphazene initially forms spherical micelles (10-20 nm) by self-assembly in aqueous solution at a very low concentration (<0.1 w/w %), but nanofibers (self-assembled fibrillar networks, SAFINs) are formed by self-assembly from the micelles when the concentration is equal to or greater than about 1 w/w %. Thus, the compound of Formula 1 can afford to form molecular hydrogel with excellent mechanical strength at a low concentration of less than 2 w/w % (refer to Experimental Example 2 below). Furthermore, the hydrogel has thermosensitivity, biodegradability, and compatibility with peptide and protein drugs, and exhibits a sustained release property without any burst effect in the early stage of intravenous injection. Thus, the hydrogel formed from the compound of Formula 1 and water may be efficiently used for drug delivery.

According to another aspect of the present invention, there is provided a drug carrier including the cyclotriphosphazene of Formula 1.

The drug carrier may be in the form of a hydrogel including the compound of Formula 1. The drug carrier may be prepared using a method that is conventionally used to prepare drug carriers using a hydrogel. The hydrogel contained in the drug carrier may include 0.1 w/w % or more, for example, 0.5 to 5 w/w % of the compound of Formula 1. The hydrogel is a thermosensitive gel that rapidly gelates at about 30° C. and has a viscosity of about $1.0 \times 10^5$ Pas at around body temperature (refer to Experimental Example 1-(2) below). Accordingly, the drug carrier including the compound of Formula 1 may gelate in the body to exhibit a sustained release of a drug contained therein.

In addition, the compound of Formula 1 was found to form a hydrogel very quickly in aqueous solution. While the procedure to prepare conventional organic polymer gels is complex and time-consuming (days), the hydro-gel from the compound of Formula 1 (refer to Experimental Example 1-(3) below) may be quickly prepared (within 30 minutes) by a simple procedure. For example, the compound of Formula 1 in water (1-2 w/w %) is heated with stirring to a temperature in the range of 60 to 80° C. to obtain a translucent gel, which is cooled to room temperature to obtain a clear sol (refer to Experimental Example 1-(3) below). Therefore, the drug carrier including the compound of Formula 1 may be simply prepared.

In addition, the drug carrier is effective for a sustained release of a protein drug and does not denature protein so as to be efficiently used for delivery of a protein drug including peptide. Furthermore, the drug carrier does not exhibit any burst effect of a drug during the early stage of the sustained release of the drug, and thus may be efficiently used for a sustained release of the drug. Furthermore, the drug carrier exhibits a zero-order release profile indicating an ideal drug release pattern. The drug carrier may also delay a drug release rate by increasing the concentration of the compound of Formula 1 contained in the hydrogel (refer to Experimental Example 3 below).

The hydrogel prepared using the compound of Formula 1 according to the present invention may be used as various bio-materials in tissue engineering or the like in addition to the drug carrier.

Advantageous Effects

As described above, the compound of Formula 1 according to an embodiment of the present invention may form a strong hydrogel at a very low concentration of 2 w/w % or less, while the conventional organic polymers may form a hydrogel at a very high concentration ranging from 15 to 30 w/w %. Furthermore, the hydrogel prepared using the compound of Formula 1 exhibits biodegradability, thermosensitivity at around body temperature, biocompatibility with protein drugs, and an easy way to prepare along with a sustained release property without any burst effect in the early stage of release. Therefore, the present cyclotriphosphazene molecular hydrogel may be efficiently used as a drug carrier for a sustained release of a drug, particularly, a protein drug.

MODE OF THE INVENTION

The present invention will be described in further detail with reference to the following examples. These examples are for illustrative purposes only and are not intended to limit the scope of the present invention.

Experimental Equipment

Elementary analysis was performed on carbon, hydrogen, and nitrogen by using a Carlo Erba-EA1108C, H, N analyzer in the following examples. Meanwhile, a nuclear magnetic resonance (NMR) spectrum of hydrogen was measured using a Bruker DPX-250 NMR Spectromter, and an NMR spectrum of phosphorus was measured using a Varian INOVA-500 NMR Spectrometer.

Example 1

Preparation of tris(methoxypolyethylene glycol350) tris[carbobenzyloxylysyl-aspartylbis(diethylaspartate)]cyclotriphosphazene, [NP(PEG350)(N$^\alpha$-Cbz-LysAsp (AspEt$_2$)$_2$)]$_3$ (1)

1.60 g (4.58 mmol) of methoxypolyethylene glycol having a molecular weight of 350 and 0.13 g (5.65 mmol) of a piece of sodium metal were added to an anhydrous tetrahydrofuran solvent and the mixture was refluxed in an argon atmosphere for 48 hours to produce a sodium salt of methoxypolyethylene glycol. Meanwhile, 0.50 g (1.44 mmol) of hexachlorocyclotriphosphazene was dissolved in an anhydrous tetrahydrofuran solvent and the solution was cooled in a dry ice-acetone bath (−78° C.). Then, a solution of the prepared sodium salt of methoxypolyethylene glycol was slowly added thereto. After 4 hours, the dry ice-acetone bath was removed and the reaction solution was further reacted at room temperature for 8 hours. To this solution was added a solution (100 ml) of 2.61 g (25.80 mmol) of triethylamine and 4.90 g (6.65 mmol) of a dendritic carbobenzyloxylysylaspartylbis(diethylaspartate) ($N^\alpha$-Cbz-LysAsp(AspEt$_2$)$_2$) dissolved in chloroform were added. Then, the reaction mixture was reacted at room temperature for 12 hours and further reacted at 70° C. for 72 hours. After the reaction was completed, the resultant reaction mixture was filtered to remove precipitated byproducts (Et$_3$NHCl or NaCl), and the filtrate was concentrated under reduced pressure to obtain a dark brown solid-like substance, which was purified by column chromatography using a silica gel (60-100 mesh) column and methylene chloride including 9 w/w % methanol as a mobile phase. Finally, 3.68 g of a final product [NP(PEG350){$N^\alpha$-Cbz-LysAsp(AspEt$_2$)$_2$}]$_3$ was obtained (Yield: 76%). Elementary analysis and NMR analysis of the product were performed, and the results are as follows.

Molecular formula: $C_{147}H_{243}N_{18}O_{63}P_3$
Result of elementary analysis: C, 52.49; H, 7.28; N, 7.50.
Theoretical value of elementary analysis: C, 52.49; H, 7.76; N, 7.80.
$^1$H NMR spectrum (CDCl$_3$, ppm): δ 7.88 (d, 1H, NH), δ 7.65 (d, 1H, NH), δ 7.14 (m, 5H, Cbz-arom), δ 5.21 (s, 2H, CH$_2$-Cbz), δ 4.82 (m, 1H, H-Asp), δ 4.65 (m, 1H, H-Lys), 4.13 (m, 8H, CH$_2$-Asp), δ 4.12 (m, 4H, OCH$_2$-MPEG), δ 3.41-3.70 (b, 28H, CH$_2$-MPEG350), δ 3.31 (s, 3H, CH$_3$-MPEG350), δ 2.93 (m, 2H, CH$_2$ of Lys), δ 1.55 (m, 2H, CH$_2$-Lys), δ 1.12-1.21 (m, 12H, CH$_3$-Asp).
$^{31}$P NMR spectrum (CDCl$_3$, ppm): δ 22.83
Average molecular weight (Mw): 3363.51

Example 2

Preparation of tris(methoxypolyethylene glycol550) tris[carbobenzyloxylysyl-aspartylbis(diethylaspartate)]cyclotriphosphazene, [NP(PEG550)($N^\alpha$-Cbz-LysAsp-(AspEt$_2$)$_2$)]$_3$

[NP(PEG550){$N^\alpha$-Cbz-LysAsp(AspEt$_2$)$_2$}]$_3$ was prepared in the same manner as in Example 1, except that 2.51 g (4.57 mmol) of methoxypolyethylene glycol having a molecular weight of 550, 0.13 g (5.65 mmol) of a piece of sodium metal, 1.00 g (2.88 mmol) of hexachlorocyclotriphosphazene, 2.61 g (25.80 mmol) of triethyl amine, and 4.90 g (6.65 mmol) of carbobenzyloxylysylaspartylbis(diethylaspartate), ($N^\alpha$-Cbz-LysAsp(AspEt$_2$)$_2$) were used instead of the reactants used in Example 1 (Yield: 62%). Elementary analysis and NMR analysis of the product were performed, and the results are as follows.

Molecular formula: $C_{177}H_{303}N_{18}O_{78}P_3$
Result of elementary analysis: C, 53.49; H, 8.06; N, 5.76.
Theoretical value of elementary analysis: C, 52.83; H, 7.59; N, 6.26.
$^1$H NMR spectrum (CDCl$_3$, ppm): δ 7.88 (d, 1H, NH), δ 7.65 (d, 1H, NH), δ 7.14 (m, 5H, Cbz-arom), δ 5.21 (s, 2H, CH$_2$-Cbz), δ 5.02 (d, 1H, NH), δ 4.82 (m, 1H, H-Asp), δ 4.65 (m, 1H, H-Lys), δ 4.13 (m, 8H, CH$_2$-Asp), δ 4.12 (m, 4H, OCH$_2$-MPEG), δ 3.41-3.70 (b, 46H, CH$_2$-MPEG550), δ 3.31 (s, 3H, CH$_3$-MPEG550), δ 2.92 (d, 2H, CH$_2$-Lys), δ 2.65 (m, 4H, CH$_2$-Asp and CH$_2$-Lys), δ 1.55 (m, 2H, CH$_2$-Lys), δ 1.12-1.21 (m, 12H, CH$_3$-Asp).
$^{31}$P NMR spectrum (CDCl$_3$, ppm): δ 22.93
Average molecular weight (Mw): 4024.50

Example 3

Preparation of tris(methoxypolyethylene glycol750) tris[carbobenzyloxylysyl-aspartylbis(diethylaspartate)]cyclotriphosphazene, [NP(PEG750)($N^\alpha$-Cbz-LysAsp-(AspEt$_2$)$_2$)]$_3$

[NP(PEG750){$N^\alpha$-Cbz-LysAsp(AspEt$_2$)$_2$}]$_3$ was prepared in the same manner as in Example 1, except that 3.43 g (4.57 mmol) of methoxypolyethylene glycol having a molecular weight of 750, 0.13 g (5.65 mmol) of a piece of sodium metal, 0.5 g (1.44 mmol) of hexachlorocyclotriphosphazene, 2.61 g (25.80 mmol) of triethyl amine, and 4.90 g (6.65 mmol) of carbobenzyloxylysylaspartylbis(diethylaspartate) ($N^\alpha$-Cbz-LysAsp(AspEt$_2$)$_2$ were used instead of the reactants used in Example 1 (Yield: 51%). Elementary analysis and NMR analysis of the product were performed, and the results are as follows.

Molecular formula: $C_{201}H_{351}N_{18}O_{90}P_3$
Result of elementary analysis: C, 53.49; H, 8.06; N, 5.76.
Theoretical value of elementary analysis: C, 51.22; H, 8.09; N, 6.07.
$^1$H NMR analysis (CDCl$_3$, ppm): δ 7.88 (d, 1H, NH), δ 7.65 (d, 1H, NH), δ 7.14 (m, Cbz-arom), δ 5.21 (s, 2H, CH$_2$-Cbz), δ 5.02 (d, 1H, NH), δ 4.82 (m, 2H, H-Asp), δ 4.65 (m, 1H, H-Lys), δ 4.13 (m, 8H, CH$_2$-Asp), δ 4.12 (m, 4H, CH$_2$-MPEG), δ 3.41-3.70 (b, 64H, CH$_2$-MPEG750), δ 3.31 (s, 3H, CH$_3$-MPEG750), δ2.92 (d, 2H, CH$_2$-Lys), δ 2.65 (m, 4H, CH$_2$-Asp and CH$_2$-Lys), δ 1.55 (m, 2H, CH$_2$-Lys), δ 1.12-1.21 (m, 12H, CH$_3$-Asp).
$^{31}$P NMR analysis (CDCl$_3$, ppm): δ 22.93
Average molecular weight (Mw): 4549.92.

Example 4

Preparation of tris(methoxypolyethylene glycol350) tris[carbobenzyloxylysyl-glutamylbis(diethylglutamate)]cyclotriphosphazene, [NP(PEG350)($N^\alpha$-Cbz-LysGlu-(GluEt$_2$)$_2$)]$_3$

[NP(PEG350){$N^\alpha$-Cbz-LysGlu(GluEt$_2$)$_2$}]$_3$ was prepared in the same manner as in Example 1, except that 1.60 g (4.57 mmol) of methoxypolyethylene glycol having a molecular weight of 350, 0.13 g (5.65 mmol) of a piece of sodium metal, 0.50 g (1.44 mmol) of hexachlorocyclotriphosphazene, 2.61 g (25.80 mmol) of triethyl amine, and 5.18 g (6.65 mmol) of carbobenzyloxylysylglutamylbis(diethylglutamate) ($N^\alpha$-Cbz-LysGlu(GluEt$_2$)$_2$) were used instead of the reactants used in Example 1 (Yield: 68%). Elementary analysis and NMR analysis the product were performed, and the results are as follows.

Molecular formula: $C_{156}H_{261}N_{18}O_{63}P_3$
Result of elementary analysis: C, 54.19; H, 7.76; N, 6.98.
Theoretical value of elementary analysis: C, 53.69; H, 7.54; N, 7.22.
$^1$H NMR spectrum (CDCl$_3$, ppm): δ 7.88 (1H, d), δ 7.65 (1H, d), δ 7.14 (m, Cbz-arom), δ 6.02 (s, 1H, NH), δ 5.20 (s, 2H, CH$_2$—CBZ), δ 4.72 (m, 2H, H-Glu), δ 4.65 (m, 1H, H-Lys), δ 4.13 (m, 8H, CH$_2$-Glu), δ 4.10 (m, 2H, OCH$_2$-MPEG), δ 3.96 (m, 1H, H-Glu), δ 3.41-3.70 (b, 28H, CH$_2$CH$_2$O-MPEG350), δ 3.31 (s, 3H, MPEG350-OCH$_3$), δ 2.45-2.55 (m, 2H, CH$_2$ of Glu and CH$_2$-Lys), δ 2.33 (m, 6H, CH$_2$-Glu), δ 1.87 (m, 4H, CH$_2$-Glu), δ 1.55 (m, 2H, CH$_2$-Lys), δ 1.12-1.21 (m, 12H, CH$_3$-Glu).
$^{31}$P NMR spectrum (CDCl$_3$, ppm): δ 22.93
Average molecular weight (Mw): 3489.75

Example 5

Preparation of tris(methoxypolyethylene glycol550) tris[carbobenzyloxylysyl-glutamylbis(diethyl-glutamate)]cyclotriphosphazene, [NP(PEG550)(N$^α$-Cbz-LysGlu-(GluEt$_2$)$_2$}]$_3$

[NP(PEG550){N$^α$-Cbz-LysGlu(GluEt$_2$)$_2$}]$_3$ was prepared in the same manner as in Example 1, except that 2.51 g (4.57 mmol) of methoxypolyethylene glycol having a molecular weight of 550, 0.13 g (5.65 mmol) of a piece of sodium metal, 0.5 g (1.44 mmol) of hexachlorocyclotriphosphazene, 1.2 mL (16.0 mmol) of triethyl amine, and 5.18 g (6.65 mmol) of carbobenzyloxylysylglutamylbis(diethylglutamate) (N$^α$-Cbz-LysGlu(GluEt$_2$)$_2$) were used instead of the reactants used in Example 1 (Yield: 58%). Elementary analysis and NMR analysis of the product were performed, and the results are as follows.
Molecular formula: C$_{186}$H$_{321}$N$_{18}$O$_{78}$P$_3$
Result of elementary analysis: C, 53.49; H, 8.06; N, 6.32.
Theoretical value of elementary analysis: C, 53.82; H, 7.80; N, 6.07.
$^1$H NMR spectrum (CDCl$_3$, ppm): δ 7.88 (d, 1H, NH), δ 7.65 (d, 1H, NH), δ 7.24 (m, arom-Cbz), δ 5.18 (s, 2H, CH$_2$-Cbz), δ 5.02 (bs, 1H, NH), δ 4.72 (m, 2H, H-Glu), δ 4.65 (m, 1H, H-Lys), δ 4.13 (m, 8H, OCH$_2$-Glu), δ 4.10 (m, 2H, OCH$_2$-MPEG), δ 3.96 (m, 1H, H-Glu), δ 3.41-3.72 (b, 48H, CH$_2$CH$_2$O-MPEG550), δ 3.31 (s, 3H, MPEG350-OCH$_3$), δ 2.45-2.55 (m, 2H, CH$_2$ of Glu and CH$_2$-Lys), δ 2.33 (m, 6H, CH$_2$-Glu), δ 1.87 (m, 4H, CH$_2$-Glu), δ 1.55 (m, 2H, CH$_2$-Lys), δ 1.12-1.21 (m, 12H, CH$_3$-Glu).
$^{31}$P NMR spectrum (500 MHz, CDCl$_3$, 25C): δ 22.98
Molecular weight: 4150.53

Example 6

Preparation of tris(methoxypolyethylene glycol750) tris[carbobenzyloxylysyl-glutamylbis(diethyl-glutamate)]cyclotriphosphazene, [NP(PEG750)(N$^α$-Cbz-LysGlu-(GluEt$_2$)$_2$}]$_3$

[NP(PEG750){N$^α$-Cbz-LysGlu(GluEt$_2$)$_2$}]$_3$ was prepared in the same manner as in Example 1, except that 3.43 g (4.57 mmol) of methoxypolyethylene glycol having a molecular weight of 750, 0.13 g (5.65 mmol) of a piece of sodium metal, 0.5 g (1.44 mmol) of hexachlorocyclotriphosphazene, 1.2 mL (16.0 mmol) of triethyl amine, and 5.18 g (6.65 mmol) of carbobenzyloxylysylglutamylbis(diethylglutamate) (N$^α$-Cbz-LysGlu(GluEt$_2$)$_2$) were used instead of the reactants used in Example 1 (Yield: 60%). Elementary analysis and NMR analysis of the product were performed, and the results are as follows.
Molecular formula: C$_{210}$H$_{383}$N$_{18}$O$_{60}$P$_3$
Result of elementary analysis: C, 53.49; H, 8.06; N, 5.76.
Theoretical value of elementary analysis: C, 53.62; H, 7.89; N, 5.44.
$^1$H NMR spectrum (CDCl$_3$, ppm): δ 7.88 (d, 1H, NH), δ 7.65 (d, 1H, NH), δ 7.24 (m, arom-Cbz), δ 5.18 (s, 2H, CH$_2$-Cbz), δ 5.02 (d, 1H, NH), δ 4.72 (m, 2H, H-Glu), δ 4.65 (m, 1H, H-Lys), δ 4.13 (m, 8H, OCH$_2$-Glu), δ 4.10 (m, 2H, OCH$_2$-MPEG), δ 3.96 (m, 1H, H-Glu), δ 3.41-3.72 (b, 64H, CH$_2$CH$_2$O-MPEG750), δ 3.31 (s, 3H, MPEG750-OCH$_3$), δ 2.45-2.56 (m, 4H, CH$_2$-Glu, and CH$_2$-Lys), δ 2.33 (m, 6H, CH$_2$-Glu), δ 1.87 (m, 4H, CH$_2$-Glu), δ 1.55 (m, 2H, CH$_2$-Lys), δ 1.12-1.21 (m, 16 12H, CH$_3$-Glu),
$^{31}$P NMR spectrum (CDCl$_3$, ppm): δ 22.93
Average molecular weight (Mw): 4724.50

Example 7

Preparation of tris(methoxypolyethylene glycol350) tris[carbobenzyloxylysyl-aminomalonylbis(diethyl-malonate)]cyclotriphosphazene, [NP(PEG350)(N$^α$-Cbz-LysMal-(MalEt$_2$)$_2$}]$_3$

[NP(PEG350){N$^α$-Cbz-LysMal(MalEt$_2$)$_2$}]$_3$ was prepared in the same manner as in Example 1, except that 1.60 g (4.57 mmol) of methoxypolyethylene glycol having a molecular weight of 350, 0.13 g (5.65 mmol) of piece of sodium metal, 1.00 g (2.88 mmol) of hexachlorocyclotriphosphazene, 1.2 mL (16.0 mmol) of triethyl amine, and 4.46 g (6.65 mmol) of carbobenzyloxylysylaminomalonylbis(diethylmalonate) (N$^α$-Cbz-LysMal(MalEt$_2$)$_2$) were used instead of the reactants used in Example 1 (Yield: 71%). Elementary analysis and NMR analysis of the product were performed, and the results are as follows.
Molecular formula: C$_{138}$H$_{225}$N$_{18}$O$_{63}$P$_3$
Result of elementary analysis: C, 51.89; H, 7.76; N, 7.96.
Theoretical value of elementary analysis: C, 51.20; H, 7.01; N, 7.79.
$^1$H NMR spectrum (CDCl$_3$, ppm): δ 7.88 (1H, d-NH), δ 7.65 (1H, d-NH), δ 7.14 (m, Cbz-arom), δ 6.02 (s, 1H, NH), δ 5.48 (s, 2H, CH-Mal), δ 5.34 (s, 2H, CH$_2$—CBZ), δ 5.26 (s, 2H, CH-Mal), δ 4.45 (m, 1H, H-Lys), δ 4.12 (m, 8H, CH$_2$-Mal), δ3.41-3.70 (b, 28H, CH$_2$CH$_2$O-MPEG350), δ 3.31 (s, 3H, MPEG350-OCH$_3$), δ 2.65 (m, 2H, CH$_2$-Lys), δ 1.55 (m, 2H, CH$_2$-Lys), δ 1.21 (t, 12H, CH$_3$-Mal).
$^{31}$P NMR spectrum (CDCl$_3$, ppm): δ 22.73
Average molecular weight (Mw): 3237.27

Example 8

Preparation of tris(methoxypolyethylene glycol550) tris[carbobenzyloxylysyl-aminomalonylbis(diethyl-malonate)]cyclotriphosphazene, [NP(PEG550)(N$^α$-Cbz-LysMal-(MalEt$_2$)$_2$}]$_3$

[NP(PEG550){N$^α$-Cbz-LysMal(MalEt$_2$)$_2$}]$_3$ was prepared in the same manner as in Example 1, except that 2.51 g (4.57 mmol) of methoxypolyethylene glycol having a molecular weight of 550, 0.13 g (5.65 mmol) of a piece of sodium metal, 1.00 g (2.88 mmol) of hexachlorocyclotriphosphazene, 1.2 mL (16.0 mmol) of triethylamine, and 4.46 g (6.65 mmol) of carbobenzyloxylysylaminomalonylbis(diethylmalonate) (N$^α$-Cbz-LysMal(MalEt$_2$)$_2$) were used instead of the reactants used in Example 1 (Yield: 68%). (Rf=0.3; 10% MeOH/CH$_2$Cl$_2$). Elementary analysis and NMR analysis of the product were performed, and the results are as follows.
Molecular formula: C$_{168}$H$_{285}$N$_{18}$O$_{78}$P$_3$
Result of elementary analysis: C, 51.89; H, 7.76; N, 7.96.
Theoretical value of elementary analysis: C, 51.76; H, 7.37; N, 6.47.
$^1$H NMR spectrum (CDCl$_3$, ppm): δ 7.88 (1H, d-NH), δ 7.65 (1H, d-NH), δ 7.14 (m, Cbz-arom), δ 6.02 (s, 1H, NH), δ 5.48 (s, 2H, CH-Mal), δ 5.34 (s, 2H, CH$_2$—CBZ), δ 5.26 (s, 2H, CH-Mal), δ 4.45 (m, 1H, H-Lys), δ 4.12 (m, 8H, CH$_2$-Mal), δ3.41-3.70 (b, 48H, CH$_2$CH$_2$O-MPEG550), δ 3.31 (s, 3H, MPEG550-OCH$_3$), δ 2.65 (m, 2H, CH$_2$-Lys), δ 1.55 (m, 2H, CH$_2$-Lys), δ 1.21 (t, 12H, CH$_3$-Mal).

$^{31}$P NMR spectrum (CDCl$_3$, ppm): δ 22.89

Average molecular weight (Mw): 3898.05

Example 9

Preparation of tris(methoxypolyethylene glycol750) tris[carbobenzyloxylysyl-aminomalonylbis(diethyl-malonate)]cyclotriphosphazene, [NP(PEG750)(N$^\alpha$-Cbz-LysMal-(MalEt$_2$)$_2$}]$_3$

[NP(PEG750){N$^\alpha$-Cbz-LysMal(MalEt$_2$)$_2$}]$_3$ was prepared in the same manner as in Example 1, except that 3.43 g (4.57 mmol) of methoxypolyethylene glycol having a molecular weight of 750, 0.13 g (5.65 mmol) of a piece of sodium metal, 0.5 g (1.44 mmol) of hexachlorocyclotriphosphazene, 1.2 mL (16.0 mmol) of triethyl amine, and 4.46 g (6.65 mmol) of carbobenzyloxylysylaminomalonylbis(diethylmalonate) (N$^\alpha$-Cbz-LysMal(MalEt$_2$)$_2$) were used instead of the reactants used in Example 1 (Yield: 62%). Elementary analysis and NMR analysis of the product were performed, and the results are as follows.

Molecular formula: C$_{189}$H$_{327}$N$_{18}$O$_{90}$P$_3$

Result of elementary analysis: C, 50.09; H, 7.96; N, 5.46.

Theoretical value of elementary analysis: C, 51.77; H, 7.52; N, 5.75.

$^1$H NMR spectrum (CDCl$_3$, ppm): δ 7.88 (1H, d-NH), δ 7.65 (1H, d-NH), δ 7.14. (m, Cbz-arom), δ 6.02 (s, 1H, NH), δ 5.48 (s, 2H, CH-Mal), δ 5.34 (s, 2H, CH$_2$—CBZ), δ 5.26 (s, 2H, CH-Mal), δ 4.45 (m, 1H, H-Lys), δ 4.12 (m, 8H, CH$_2$-Mal), δ3.41-3.70 (b, 64H, CH$_2$CH$_2$O-MPEG750), δ 3.31 (s, 3H, MPEG750-OCH$_3$), δ 2.65 (m, 2H, CH$_2$-Lys), δ 1.55 (m, 2H, CH$_2$-Lys), δ 1.21 (t, 12H, CH$_3$-Mal).

$^{31}$P NMR spectrum (CDCl$_3$, ppm): δ 22.80

Average molecular weight (Mw): 4384.62

Experimental Example 1

Gelation (1) Measuring Viscosity Depending on the Shear Rate

Sol-gel phase transition of the compound prepared in Example 2 depending on temperature was measured using a rheometer produced by Thermo-Hakke Co., Ltd. (1°, 60 mm cone).

First, 0.2 g of the compound prepared in Example 2 was added to 9.8 g of distilled water, and then was heated to 70° C. to completely dissolve the compound. Then, viscosity of the solution was measured at room temperature with changing shear rates (ṙ), and the results are shown in FIG. 1.

Figure 1:
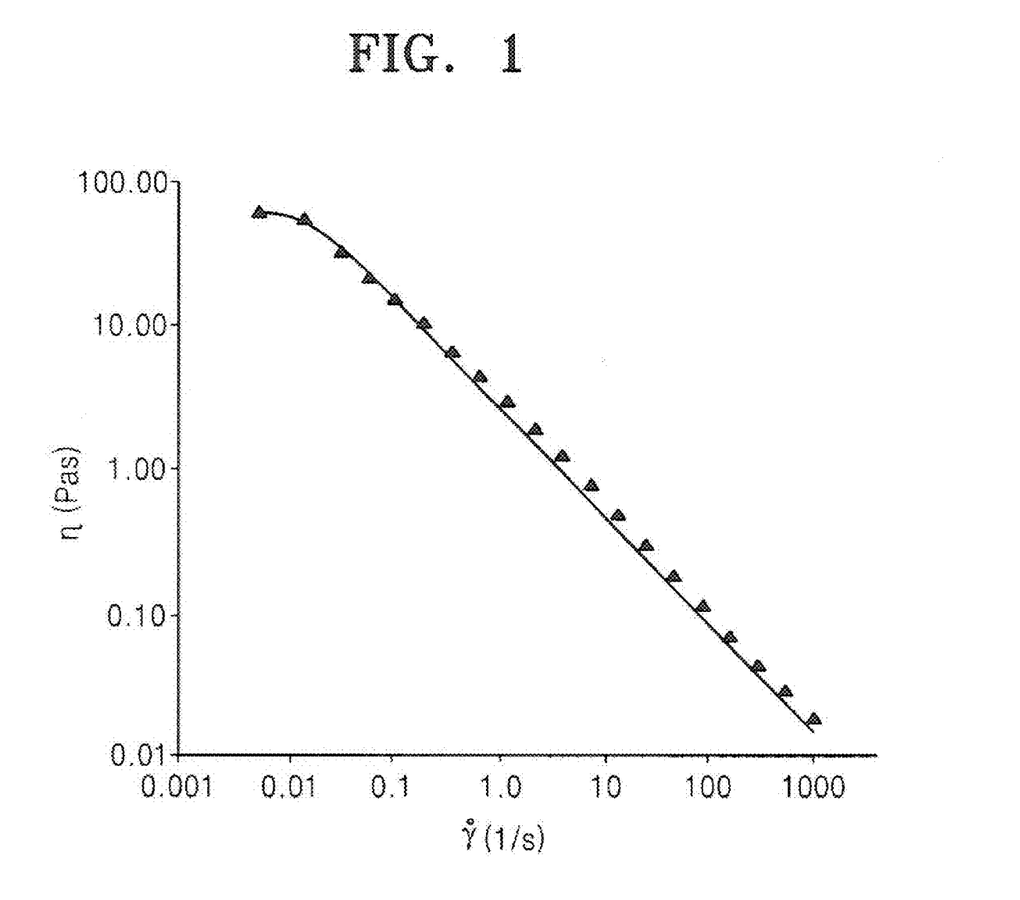
FIG. 1 is a graph illustrating viscosity of an aqueous solution of a compound according to an embodiment of the present invention of a concentration of 2 w/w % at room temperature depending on the shear rate ($\dot{r}$)

Referring to FIG. 1, at room temperature, strong shear thinning effects of viscosity were observed with increasing shear rate. Shear thinning is an effect where viscosity decreases with increasing external mechanical stimulus.

(2) Measuring Viscosity Depending on Temperature

Figure 2:
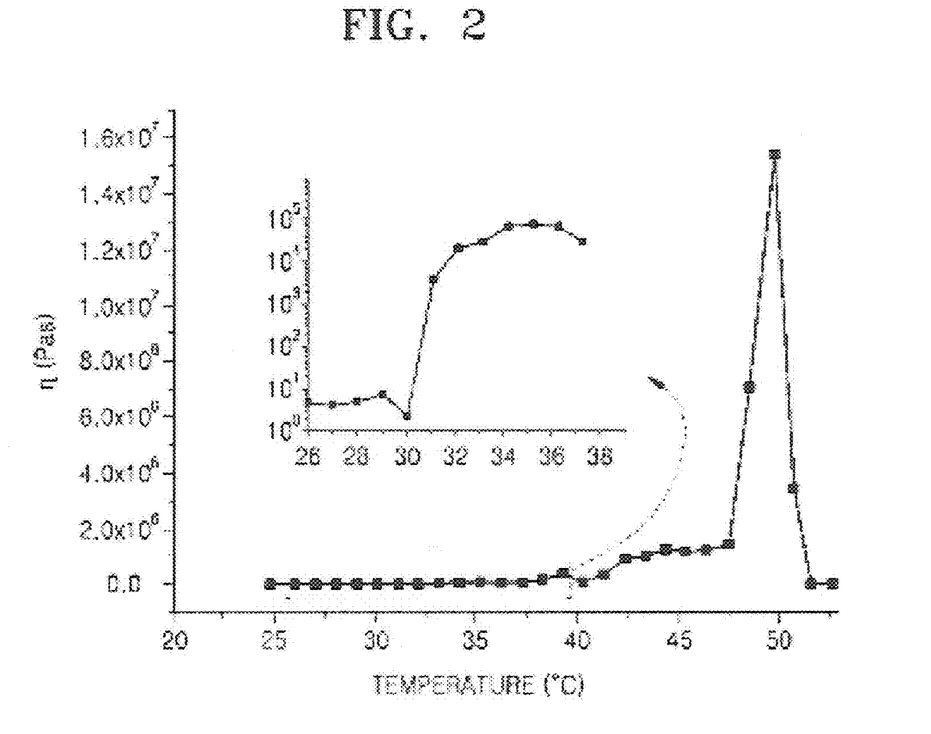
FIG. 2 is a graph illustrating viscosity of an aqueous solution of a compound according to an embodiment of the present invention of a concentration of 2 w/w % with increasing temperature by 1.0° C./min.

An aqueous solution of the compound prepared in Example 2 was prepared in the same manner as in Experimental Example 1-(1) above. Then, viscosity of the aqueous solution was measured with increasing temperature from room temperature to identify a gelation temperature and the strength change of the hydrogel. The heating rate was 1.0° C./min or 0.5° C./min and the concentration of the aqueous solution was 2 w/w %. The results are shown in FIG. 2. The temperature was increased from 5 to 75° C., but results obtained in the temperature range from 20 to 75° C. were shown. Viscosity changes in a temperature range from 26 to 39° C., i.e., body temperature range, are enlarged in a graph at the center of FIG. 2.

Referring to FIG. 2, the hydrogel had a very high maximum viscosity of 1.5×10$^7$ Pas at around 50° C. However, it was found that the viscosity is as low as about 4 Pas in the room temperature range from 20 to 30° C., but gelation starts rapidly from 30° C. and reaches a high viscosity of about 1.0×10$^5$ Pas at around body temperature according to the central graph of FIG. 2. Thus, it was identified that the compound according to the present invention was a thermosensitive gelator, which is suitable for local delivery of drugs.

Figure 3:
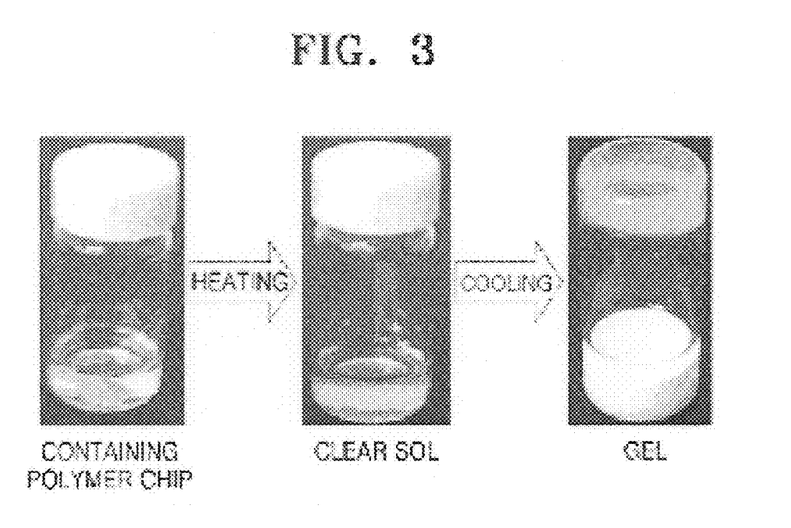
FIG. 3 shows pictures of a mixture prepared by adding a compound according to an embodiment of the present invention to distilled water at room temperature, which were taken before heating, after heating to 70° C. or higher, and after cooling to room temperature.

(3) Solubility Test According to Temperature 0.2 g of the compound prepared in Example 2 was added to 9.8 mL of water, and the solution was stirred. Then, the phase change thereof depending on temperature was observed and photographed. First, a picture of a mixture including the compound and water before heating was taken, and a picture of the mixture heated to 80° C. or higher was taken. Finally, the heated solution was cooled to room temperature, and a picture thereof was taken.

The pictures are shown in FIG. 3 in the order as described above.

Referring to FIG. 3, the compound of Formula 2 is not soluble in water at room temperature. However, the compound is dissolved into a clear sol by heating the compound to 80° C. or higher, and a clear gel was obtained by cooling the clear sol to room temperature.

According to this result, a gel may be quickly prepared by heating and cooling the compound according to the present invention. While the process for dissolution of conventional polymer gels is complex and time-consuming, the compound according to the present invention is advantageous in that it may quickly form a hydrogel (within about 30 minutes).

According to the results of Experimental Examples 1-(1) to 1-(3), the hydrogel prepared using the compound according to the present invention has viscosity that is reduced with increasing shear rate and thermosensitivity by which a gelation occurs at around body temperature, and may be very quickly prepared. Accordingly, the hydrogel prepared using the compound according to the present invention may be efficiently used for drug delivery by carrying and injecting a drug at room temperature.

Experimental Example 2

Transmission Electron Microscopic (TEM) Images Depending on Concentration

Figure 4:
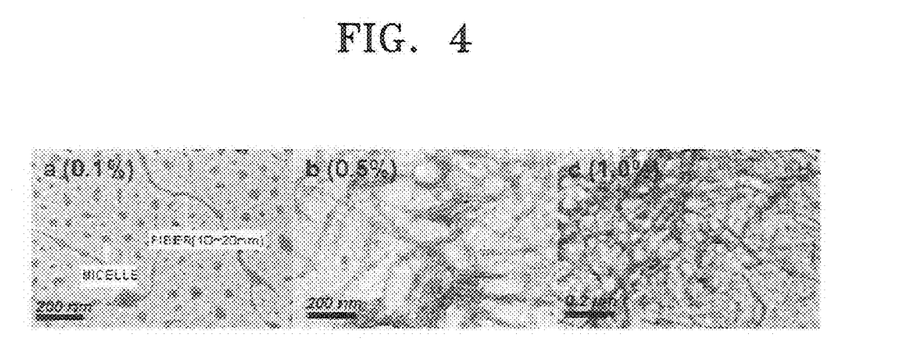
FIG. 4 shows transmission electron microscopic (TEM) images of solutions of a compound according to an embodiment of the present invention dissolved in distilled water by heat-treatment with concentrations of 0.1 w/w %, 0.5 w/w %, and 1.0 w/w %, respectively.

The compound prepared in Example 2 was dissolved in water to the concentrations of 0.1 w/w %, 0.5 w/w %, and 1.0 w/w % in the same manner as in Experimental Example 1, and TEM images of the solutions were obtained. FIG. 4 illustrates TEM images of the solutions.

Referring to FIG. 4, at a low concentration of 0.1 w/w %, the compound of Example 2 mostly exists in spherical micelles but partly starts to self-assemble into nanofibers, but at the higher concentration of 0.5 w/w %, only a fiber bundle structure was observed. In addition, a more dense and cross-linked fiber bundle structure was formed at the concentration of 1 w/w %, so that a large amount (more than 100 times the weight thereof) of water molecules may be captured by the structures. Based on this result, it was identified that a molecular hydro-gel was formed by the compound according to the present invention.

Experimental Example 3

Drug Release Test

Drug release tests were performed using albumin as a model protein drug and two different hydro-gels prepared from the compounds of Examples 2 and 3.

The albumin (Mw=78,000) that was labeled with a fluorescent material (FITC), and the hydrogels prepared from the compounds of Example 2 or 3 to different concentrations of 1, 2, or 4 w/w % were used.

Figure 5:
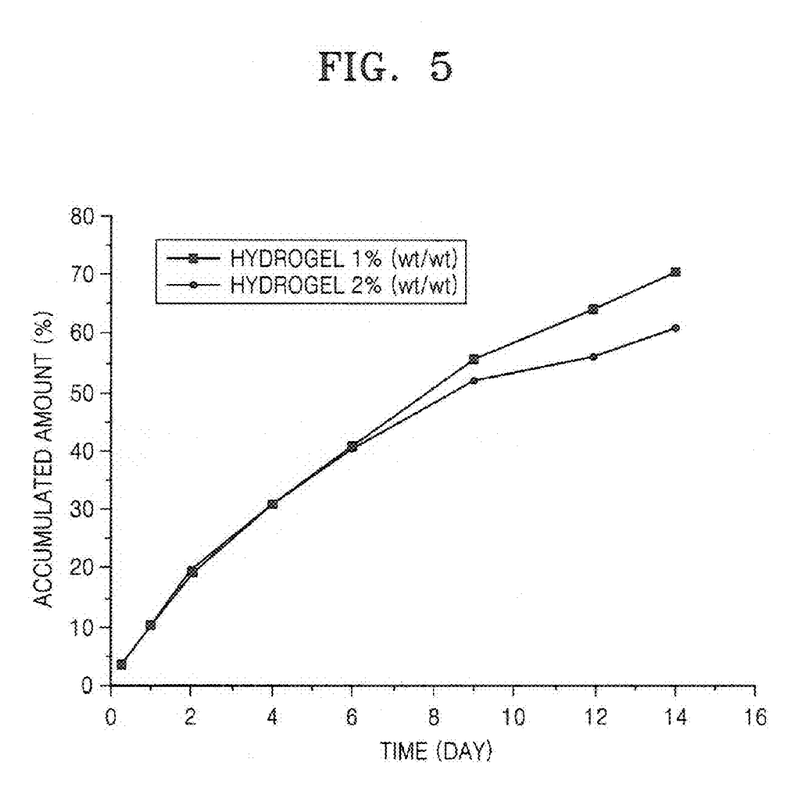
FIG. 5 is a graph illustrating amounts of fluorescent albumin released from a hydrogel, measured using a fluorescence spectrometer in a phosphate buffer solution for two weeks, wherein the hydrogel is prepared using a compound according to an embodiment of the present invention with a concentration of 1 or 2 w/w % and the fluorescent albumin.

The compound prepared in Example 2 or 3 was dissolved in 1 ml of distilled water to a desired concentration at 70° C. to prepare a homogenous sol and the solution was rapidly cooled to 37° C. A fluorescent albumin solution (2 mg/ml) (Sigma) was mixed with the solution to obtain a homogenous sol in a vial and the sol was maintained until it turned to a hydrogel. If the hydrogel is formed, 6 ml of a phosphate buffer solution (PBS) was added to the hydrogel in the vial, which was slowly shaken in a constant temperature bath at 37° C. A small amount (100 μl) of each sample solution was taken from the vial at predetermined time and analyzed using a fluorescence spectrometer to measure the amount of the fluorescent albumin released from the hydrogel. The test was performed for 2 weeks. FIG. 5 shows the result of the compound prepared in Example 2, and FIG. 6 shows the result of the compound prepared in Example 3.

Figure 6:
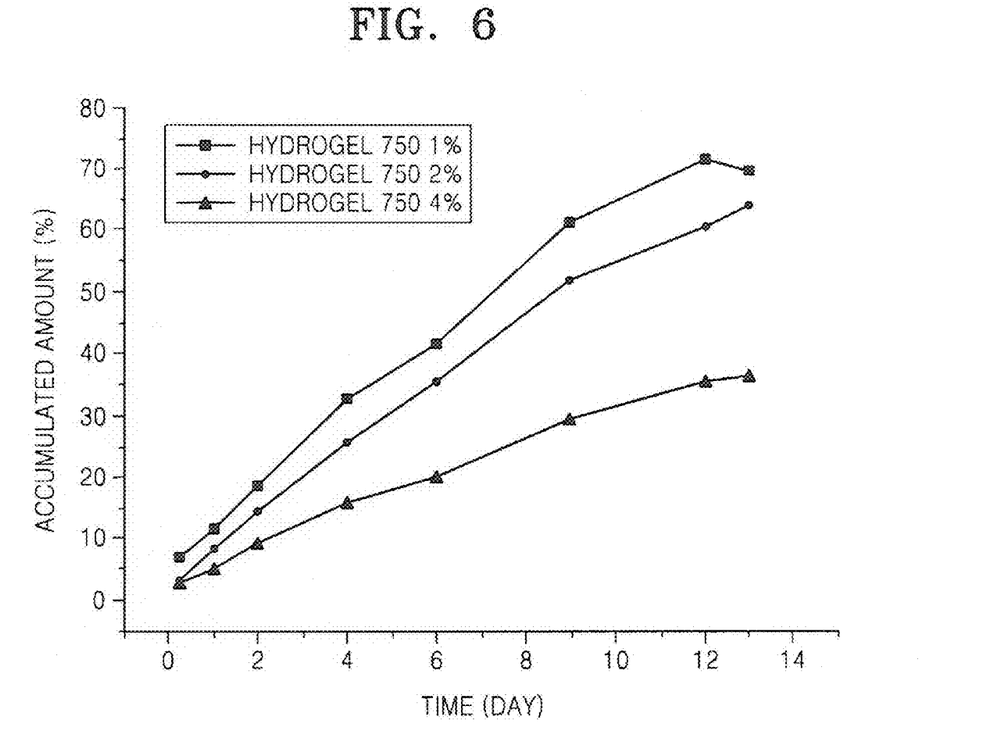
FIG. 6 is a graph illustrating amounts of fluorescent albumin released from a hydrogel, measured using a fluorescence spectrometer in a phosphate buffer solution for two weeks, wherein the hydrogel is prepared by adding a compound according to an embodiment of the present invention to distilled water to a concentration of 1, 2, or 4 w/w %, heating the solution to 70° C. to obtain a homogenous sol, rapidly cooling the sol to 37° C., adding a fluorescent albumin solution to the sol, and cooling the mixture to room temperature.

As shown in FIG. 5 and FIG. 6, a burst effect was not observed at the early stage of release and a zero-order release was observed for 2 weeks. In addition, referring to FIG. 6, the drug release rate may be controlled by regulating the concentration of the hydrogel.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A cyclotriphosphazene represented by Formula 1 below:

Formula 1 where n is 7, 12, or 16,
x is 0, 1, or 2, and
R is each independently a C1-C6 alkyl or benzyl.

2. The cyclotriphosphazene of claim 1, wherein the cyclotriphosphazene is selected from the group consisting of
tris(methoxypolyethylene glycol350)tris[carbobenzyloxylysylaspartylbis-(diethylaspartate)]cyclotriphosphazene,
tris(methoxypolyethylene glycol550)tris[carbobenzyloxylysylaspartylbis-(diethylaspartate)]cyclotriphosphazene,
tris(methoxypolyethylene glycol750)tris[carbobenzyloxylysylaspartylbis-(diethylaspartate)]cyclotriphosphazene,
tris(methoxypolyethylene glycol350)tris[carbobenzyloxylysylglutamylbis-(diethylglutamate)]cyclotriphosphazene,
tris(methoxypolyethylene glycol550)tris[carbobenzyloxylysylglutamylbis-(diethylglutamate)]cyclotriphosphazene,
tris(methoxypolyethylene glycol750)tris[carbobenzyloxylysylglutamylbis-(diethylglutamate)]cyclotriphosphazene,
tris(methoxypolyethylene glycol350)tris[carbobenzyloxylysylaminomalonylbis-(diethylmalonate)]cyclotriphosphazene,
tris(methoxypolyethylene glycol550)tris[carbobenzyloxylysylaminomalonylbis-(diethylmalonate)]cyclotriphosphazene, and
tris(methoxypolyethylene glycol750)tris[carbobenzyloxylysylaminomalonylbis-(diethylmalonate)]cyclotriphosphazene.

3. A method of preparing the cyclotriphosphazene represented by Formula 1 according to claim 1, the method comprising the reaction of a cyclotriphosphazene represented by Formula 5 below bearing polyethylene glycol and chlorine with an ester of a dendritic tetrapeptide represented by Formula 6 below:

[Formula 5]

where $R^1$ is $-(CH_2CH_2O)_nCH_3$, and

[Formula 6]

where x and R are defined in claim 1.

4. The method of claim 3, wherein the reaction is performed in the presence of triethylamine.

5. The method of claim 3, wherein the compound of Formula 5 is prepared by reaction of hexachlorocyclotriphosphazene represented by Formula 4 with a metal salt of methoxypolyethylene glycol represented by Formula 3 below:

[Formula 4]

[Formula 3]

where n is an integer selected from the group consisting of 3, 7, 12, and 16.

6. The method of claim 3, wherein the reaction is performed in a solvent selected from the group consisting of tetrahydrofuran, benzene, toluene, chloroform, and any combination thereof.

7. The method of claim 5, wherein a solution of the cyclochlorotriphosphazene of Formula 4 is cooled to a low temperature of −20° C. or less and a solution of the methoxy polyethylene glycol salt of Formula 3 is slowly added thereto.

8. A drug carrier comprising a cyclotriphosphazene represented by Formula 1 according to claim 1.

9. The drug carrier of claim 8, wherein the drug carrier has a sustained release property of a drug.

10. The drug carrier of claim 8, wherein the drug carrier is used to deliver a protein drug or a peptide drug.

* * * * *

UNITED STATES PATENT AND TRADEMARK OFFICE
CERTIFICATE OF CORRECTION

PATENT NO. : 8,344,173 B2  
APPLICATION NO. : 12/990089  
DATED : January 1, 2013  
INVENTOR(S) : Sohn et al.

Page 1 of 1

It is certified that error appears in the above-identified patent and that said Letters Patent is hereby corrected as shown below:

Cover Page, Column 1, Item (22) should appear as follows:

(22)    PCT Filed:    April 27, 2009

Signed and Sealed this  
Fifth Day of March, 2013

Teresa Stanek Rea  
*Acting Director of the United States Patent and Trademark Office*